(12) United States Patent
Brewer et al.

(10) Patent No.: US 8,517,019 B2
(45) Date of Patent: Aug. 27, 2013

(54) METHOD AND APPARATUS FOR METERED DOSE DISPENSING

(75) Inventors: Richard D. Brewer, Loughborough (GB); Peter D. Hodson, Loughborough (GB); Graham R. Purkins, Loughborough (GB); David J.C. Steven, Loughborough (GB)

(73) Assignee: 3M Innovative Properties Company, St. Paul, MN (US)

( * ) Notice: Subject to any disclaimer, the term of this patent is extended or adjusted under 35 U.S.C. 154(b) by 1053 days.

(21) Appl. No.: 12/281,559

(22) PCT Filed: Mar. 1, 2007

(86) PCT No.: PCT/US2007/063043
§ 371 (c)(1),
(2), (4) Date: Nov. 10, 2008

(87) PCT Pub. No.: WO2007/103712
PCT Pub. Date: Sep. 13, 2007

(65) Prior Publication Data
US 2009/0308385 A1    Dec. 17, 2009

Related U.S. Application Data

(60) Provisional application No. 60/743,397, filed on Mar. 3, 2006.

(51) Int. Cl.
*A62B 7/00* (2006.01)
*A62B 9/00* (2006.01)
*A61M 11/00* (2006.01)

(52) U.S. Cl.
USPC .................. 128/205.23; 128/200.23

(58) Field of Classification Search
USPC ............ 128/200.19, 200.23, 200.14, 203.15, 128/205.23; 222/19, 23; 239/71
See application file for complete search history.

(56) References Cited

U.S. PATENT DOCUMENTS

| | | | |
|---|---|---|---|
| 5,349,945 | A | 9/1994 | Wass et al. |
| 5,544,647 | A | 8/1996 | Jewett et al. |
| 6,029,659 | A | 2/2000 | O'Connor |

(Continued)

*Primary Examiner* — Jackie Ho
*Assistant Examiner* — Peter S Vasat

(57) ABSTRACT

This application discloses a dose counter device of the type for use on an aerosol dispensing assembly having an aerosol container and an actuator. The dose counter device is used for indicating the release of a dose of aerosol medication caused by the application of a force, in an axial direction, on the aerosol dispensing assembly. The dose counter device has a cap, a slider and a first counter ring. The cap is moved in a first direction along an axis of the container, which causes movement of the slider in a first linear direction laterally, relative to the axis of the container, as a function of the movement of the cap in the first direction. The first counter ring is rotated through a first arc in a first circumferential direction about the axis of the container, as a function of the movement of the slider in the first linear direction. The cap is then moved in a second opposite direction, which causes the slider to move in a second opposite linear direction, which in turn causes rotation of the first counter ring through a second arc in the first circumferential direction about the axis of the container. A sum of the first and second arcs of movement of the first counter ring defines a circumferential extent of movement of the first counter ring relative to the cap that indicates a single dose of aerosol medication dispensed from the container.

21 Claims, 16 Drawing Sheets

(56) References Cited

U.S. PATENT DOCUMENTS

Figure 4:
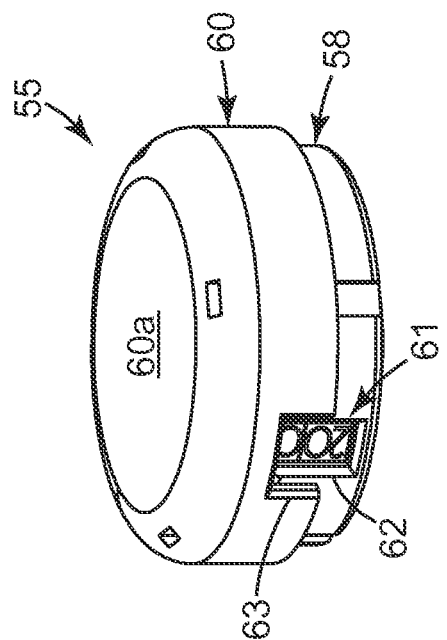

| | | | |
|---|---|---|---|
| 6,102,179 A * | 8/2000 | Hodson et al. | 192/46 |
| 6,164,494 A * | 12/2000 | Marelli | 222/38 |
| 6,701,917 B2 * | 3/2004 | O'Leary | 128/200.23 |
| 6,752,153 B1 * | 6/2004 | Eckert | 128/205.23 |
| 6,953,039 B2 | 10/2005 | Scarrott et al. | |
| 2004/0149772 A1 * | 8/2004 | Ouyang | 222/36 |
| 2004/0149773 A1 * | 8/2004 | Ouyang et al. | 222/36 |
| 2004/0255935 A1 * | 12/2004 | Bruna | 128/200.23 |

* cited by examiner

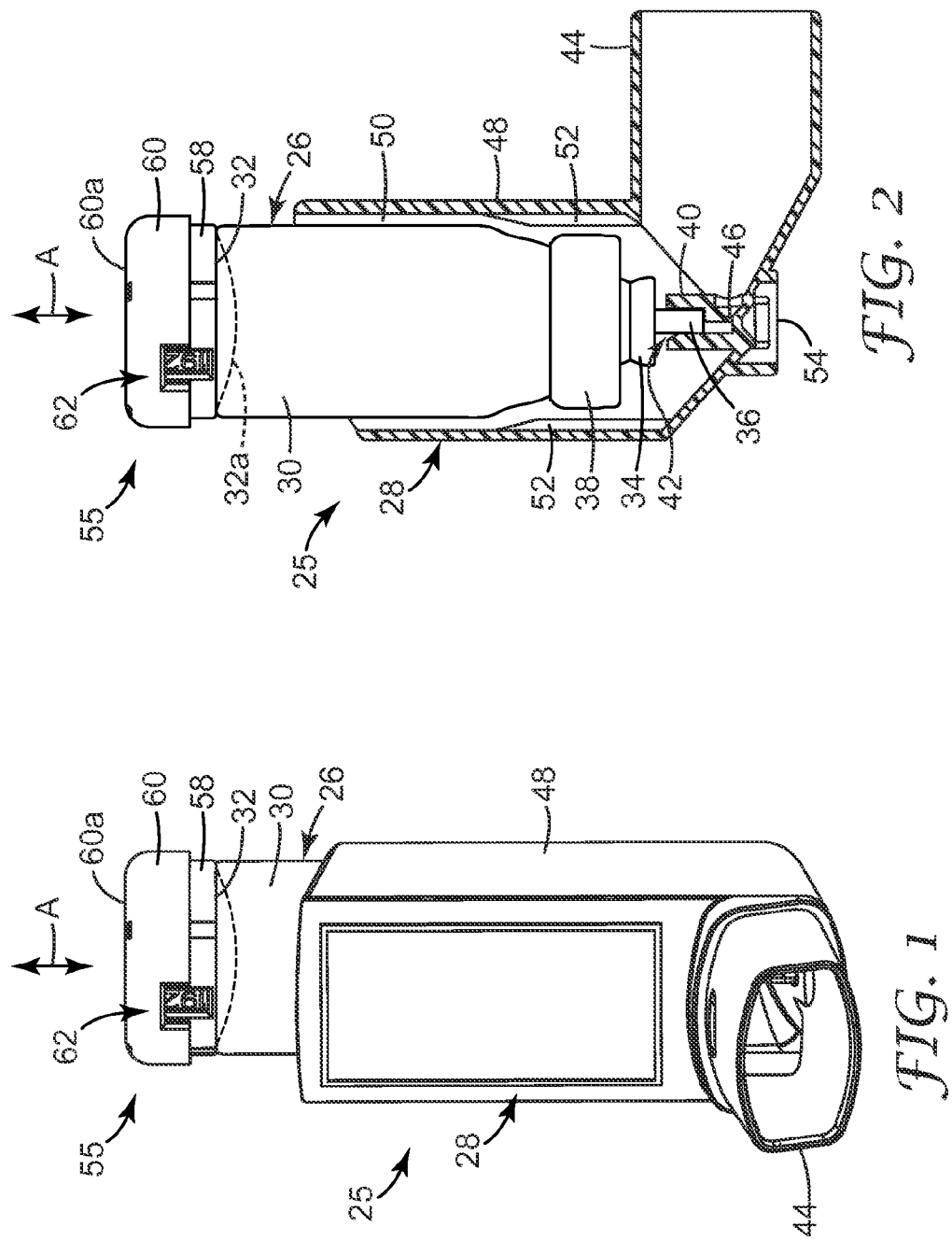

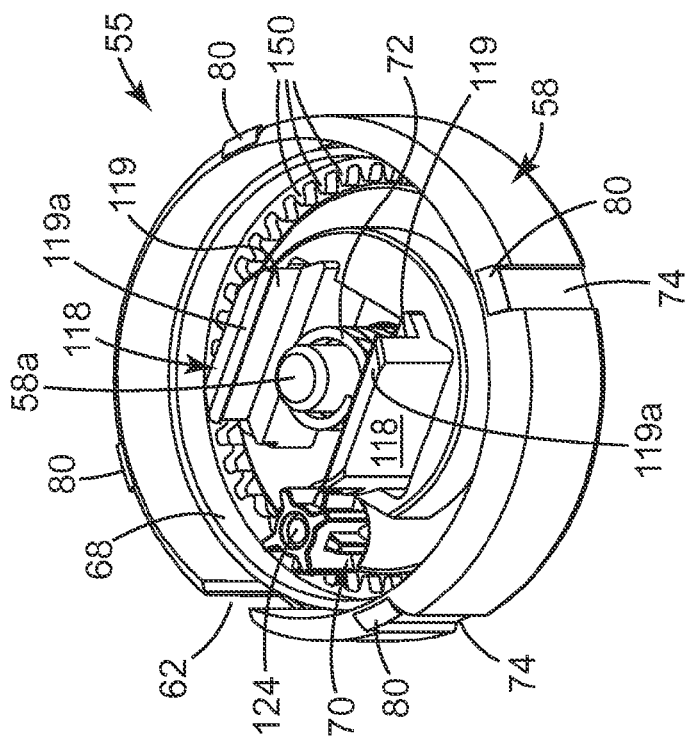
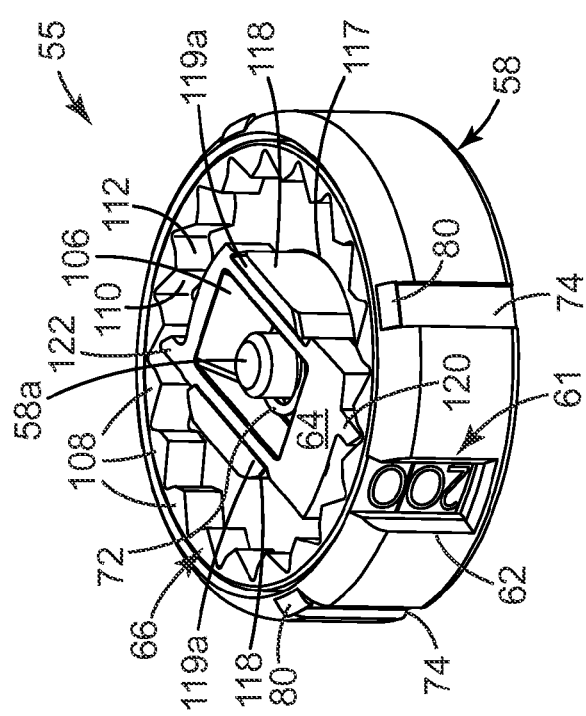

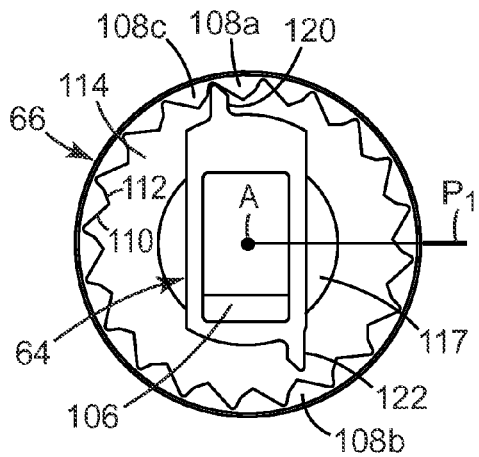
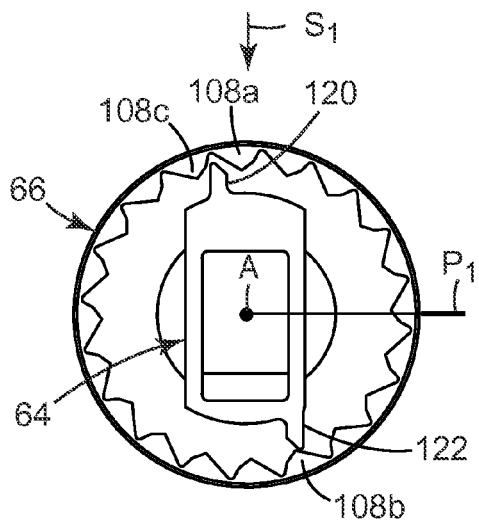
FIG. 13A    FIG. 13B
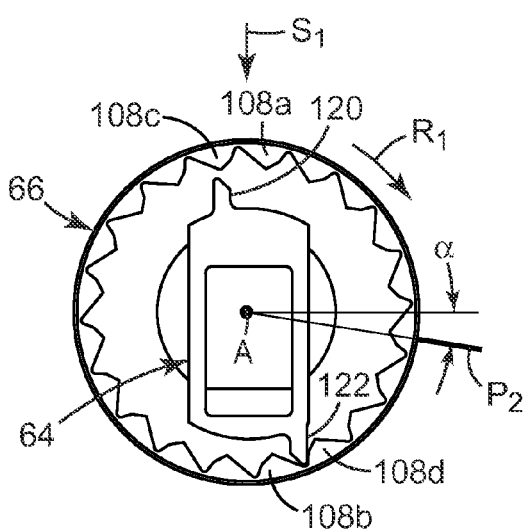
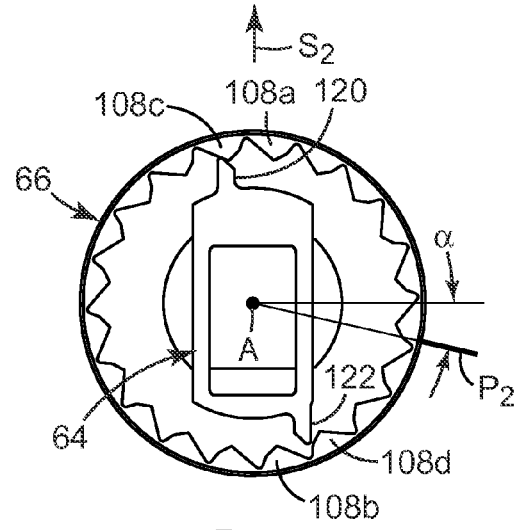
FIG. 13C    FIG. 13D
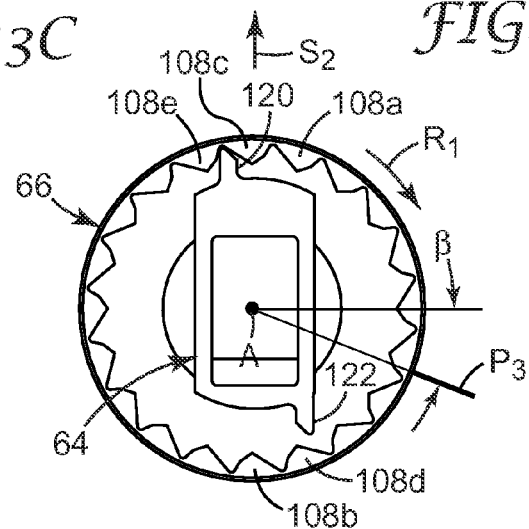
FIG. 13E

METHOD AND APPARATUS FOR METERED DOSE DISPENSING

CROSS REFERENCE TO RELATED APPLICATIONS

This application is a national stage filing under 35 U.S.C. 371 of PCT/US2007/063043 filed Mar. 1, 2008 which claims priority Provisional Application No. 60/743,397 filed Mar. 3, 2006 the disclosure of which is incorporated by reference in its/their entirety herein.

BACKGROUND

The present invention relates to monitoring the number of doses of aerosol medication dispensed from an aerosol dispensing assembly. In particular, the invention relates to a dose counter device of the type adapted to be used on an aerosol dispensing assembly, as well as to a method of counting doses of aerosol medication dispensed from such an assembly.

Metered medication dose dispensers, known as "inhalers", are commonly used for the treatment of asthma and other respiratory conditions. Metered dose dispensers typically take the form of an aerosol dispensing assembly having an aerosol container and a housing for receiving that container. The container includes medicament that is formulated with a suitable propellant that is filled into the container to define an aerosol vial. The container is typically equipped with a dispensing means, fitted by means of a ferrule, such as a valve, in particular, a metered dose valve, comprising an elongate outlet member (e.g., a valve stem) movable between closed and discharge positions, and thus defines a medication dispensing canister. The canister is not refillable, and is disposed of once the medication therein has been dispensed. The dispensing canister is typically used in conjunction with an actuator or housing (which may be reusable) that has a patient port (e.g., a mouthpiece or a port adapted for nasal use). The actuator typically comprises a support block that has a socket adapted to receive the outlet member of the valve on the container, and has an orifice in communication with the socket and the patient port. The dispensing canister and the support block are reciprocally movable relative to each other along an axis to allow the outlet member to move to its discharge position during the operation or firing of the device, thereby dispensing a dose of the medicament from the container. The actuator also typically includes an elongate portion extending opposite the support block and providing a chamber to house at least a portion of the container. There are many related design features of the actuator and the dispensing canister that are employed in order to achieve the desired medicament dispensing performance (i.e., the dispensing of one metered amount or dose of sprayed medication of appropriate particle size distribution each time the dispenser is actuated by a user).

To dispense a dose of medication, an inhaler user normally squeezes or pushes down on the inhaler in an axial direction causing a relative movement of the canister into the actuator towards the support block. It is useful for an inhaler user to know how many doses remain in his or her inhaler (i.e., how much medicament by dosage is in the container of the aerosol dispensing assembly). To this end, a reliable dose counter device and methodology is desired, in order to register how many doses have been dispensed from an aerosol dispensing assembly and in order to inform a user how many more doses still remain to be dispensed. Aerosol dispensing assemblies can vary in configuration, and it would be desirable to provide a dose counter device which is generally universally usable with the various aerosol dispensing assemblies available, and in particular with varying aerosol containers of medications that are available.

SUMMARY

In one aspect, the present invention is a dose counter device of the type for use on an aerosol dispensing assembly, wherein the dose counter device is for indicating the release of a dose of aerosol medication caused by the application of a force, in an axial direction, on the aerosol dispensing assembly. The dose counter device comprises a base, a cap coupled to the base for axial, non-rotational movement with respect to the base, with the cap having a peg thereon extending toward the base, and a spring disposed between the base and the cap to bias the cap axially away from the base. The dose counter device also comprises a slider non-rotatably disposed relative to the peg, the slider having two fingers projecting from opposite ends thereof, and the slider and the peg having cooperating facing sliding surfaces whereby axial movement of the cap relative to the base causes lateral movement of the slider relative to the base. The dose counter device further comprises a first counter ring rotatably disposed relative to the base, with the first counter ring having an inner surface comprising teeth that are engageable by the fingers of the slider acting alternately to cause indexed rotation of the first counter ring with respect to the base. For use of the device on an aerosol dispensing assembly, the base or the cap is mountable to the assembly. The present invention is adapted for use with aerosol dispensing assemblies comprising an aerosol container having a nozzle end and a closed end, and the base or the cap, as applicable, may be suitably adapted to be mounted to the closed end of the container. Alternatively, for assemblies further comprising a housing for the container, the base or the cap, as applicable, may be suitably adapted to be mounted to the housing. In an alternative embodiment, the base or the cap, as applicable, may be adapted to be mounted to an external end of the housing that is opposite to the closed end of the container.

For aerosol dispensing assemblies comprising an aerosol container having a nozzle end and a closed end and a housing therefor, it has been found to be advantageous in terms of handling and ease of operation by the user as well as ease in manufacturing and cost effectiveness to provide a dose counter mountable on or integral to the housing at a position generally opposite to the closed end of the container, as well as an assembly having such a dose counter on its container-housing in such a manner. Thus, further aspects of the present invention, independent of and separate from the first aspect, are the provision of a mechanical dose counter device for use with an aerosol dispensing assembly comprising an aerosol container having a nozzle end and a closed end and a housing therefore and for counting doses of an aerosol medication dispensed from the aerosol dispensing assembly, said dispensing caused by an application of a force in an axial direction on said assembly, wherein the dose counter device is operable by application of a force in the axial direction to the assembly (more particularly in an axial direction to the container) and wherein the dose counter device is adapted to be mounted to an external end of the housing that is opposite to the closed end of the container as well as a housing for use in such assemblies having such an operable dose counter device mounted to or integral with said external end of the housing and an aerosol dispensing assembly having such an operable dose counter device mounted to or integral with the external end of its housing.

In another aspect, the present invention comprises a method of counting doses of an aerosol medication dispensed from an aerosol dispensing assembly, said dispensing caused by an application of a force in an axial direction on said assembly, comprising the steps of moving a cap in a first direction along the axis of the aerosol dispensing assembly, moving a slider in a first linear direction laterally, relative to the axis, as a function of the movement of the cap in the first direction, and rotating a first counter ring through a first arc in a first circumferential direction about the axis, as a function of the movement of the slider in the first linear direction. The method further comprises the steps of moving the cap in a second opposite direction along the axis, moving the slider in a second opposite linear direction as a function of the movement of the cap in the second direction, and rotating the first counter ring through a second arc in the first circumferential direction about the axis, as a function of the movement of the slider in the second linear direction. A sum of the first and second arcs of movement of the first counter ring defines a circumferential extent of movement of the first counter ring relative to the cap that indicates a single dose of aerosol medication dispensed from the container.

BRIEF DESCRIPTION OF THE DRAWINGS

The present invention will be further explained with reference to the attached figures, wherein like structure or system elements are referred to by like reference numerals throughout the several views.

FIG. 1 is an isometric view of an aerosol dispensing assembly having an exemplary dose counter device in accordance with the present invention thereon.

FIG. 2 is a partial sectional view of an aerosol dispensing assembly having a slightly different housing having an exemplary dose counter device in accordance with the present invention thereon.

FIG. 3 is a side elevational view of an exemplary dose counter device in accordance with the present invention from a side showing the dose counter indicia.

FIG. 4 is an upper isometric view of the exemplary dose counter device shown in FIG. 3, also from a view showing the dose counter indicia.

FIG. 5 is an upper isometric view of the exemplary dose counter device shown in FIG. 3, with the cap thereof removed.

FIG. 6 is an upper isometric view of the exemplary dose counter device shown in FIG. 3, with the cap, the slider component, and a units ring component removed.

FIG. 7 is an exploded view of the components of the exemplary dose counter device shown in FIG. 3, as taken from above.

FIG. 8 is an exploded view of the components of the exemplary dose counter device shown in FIG. 3, as taken from below.

FIG. 9 is a partial sectional isometric view of the cap and slider components of the exemplary dose counter device shown in FIG. 3, as taken from above.

FIG. 10 is an upper isometric view of the slider and units ring components of the exemplary dose counter device shown in FIG. 3.

FIGS. 11A, 11B, and 11C are sectional views of the cap, slider and units ring of the exemplary dose counter device shown in FIG. 3 showing their respective positions during various stages of actuation of the dose counter device.

FIGS. 12A, 12B and 12C are sectional views of the exemplary dose counter device shown in FIG. 3 showing the relationships of certain components thereof during various stages of actuation of the dose counter device.

FIGS. 13A-13E illustrate the relationship of the slider and units ring components of the exemplary dose counter device shown in FIG. 3 during various stages of actuation of the dose counter device.

FIG. 14 is an isometric view of the transfer gear and units ring components of the exemplary dose counter device shown in FIG. 3, as taken from below.

FIG. 15 is an isometric view of the transfer gear component of the exemplary dose counter device shown in FIG. 3, as taken from above.

FIG. 16 is an isometric view of the base component of the exemplary dose counter device shown in FIG. 3, as taken from above.

FIGS. 17A-17E illustrate a first aspect of the relationship between the units ring and transfer gear components of the exemplary dose counter device shown in FIG. 3, as rotational motion of the units ring is transferred to the transfer gear.

FIGS. 18A-18E illustrate a second aspect of the relationship between the units ring and transfer gear components of the exemplary dose counter device shown in FIG. 3, namely that except for when the transfer gear is allowed to rotate relative to the units ring, the transfer gear is locked in position from further rotation even though the units ring may be rotated.

FIG. 19 is an isometric view of the transfer gear, units ring and tens ring components of the exemplary dose counter device shown in FIG. 3, as taken from below.

FIG. 20 is an isometric view of the transfer gear and tens ring component of the exemplary dose counter device shown in FIG. 3, as taken from above.

FIGS. 21A-21E illustrate the relationship between the transfer gear and tens ring components of the exemplary dose counter device shown in FIG. 3, as rotational motion of the transfer gear is transferred to the tens ring.

FIG. 22 is an isometric view of an exemplary aerosol dispensing assembly in accordance with another aspect of the present invention having an exemplary dose counter device in accordance with a further aspect of the present invention thereon.

FIG. 23 is a partial sectional view of the actuator of the aerosol dispensing assembly of FIG. 22 having an exemplary dose counter device in accordance with the present invention thereon.

While the above-identified figures set forth illustrative embodiments of the present invention, other embodiments are also contemplated, as noted in the disclosure. In all cases, this disclosure presents the invention by way of representation and not limitation. It should be understood that numerous other modifications and embodiments can be devised by those skilled in the art which fall within the scope and spirit of the principles of this invention.

DETAILED DESCRIPTION OF ILLUSTRATIVE EMBODIMENTS

Aerosol Dispensing Assembly

FIGS. 1 and 2 illustrate two similar embodiments of an aerosol dispensing assembly 25, which is commonly referred to as an inhaler. The aerosol dispensing assemblies 25 illustrated are each exemplary dispensers, which as typical, include an aerosol container or canister 26 and an actuator 28.

The aerosol canister 26 typically comprises a substantially cylindrical container 30 having a closed end 32 (which is typically concave in form) and an opposite opened end which is equipped with a medication dispensing valve 34. The dispensing valve 34 comprises a metering dose valve having an elongate outlet member 36 that is movable axially between closed and discharge positions. The dispensing valve 34 is normally mounted onto the container 30 by means of a ferrule 38.

The actuator 28 typically comprises a support block 40 having a socket 42. The outlet member 36 is received by the socket 42 and thus positioned in the support block 40. The container 30 and the support block 40 are reciprocally movable relative to each other in an axial direction, as illustrated by axis A and associated direction arrows in FIGS. 1 and 2. The actuator 28 typically includes a patient port such as a mouthpiece 44, and the support block 40 has an orifice 46 which is in open communication with the socket 42 and the mouthpiece 44. The actuator 28 also typically has an elongate portion 48 extending opposite the support block 40 and defining a generally cylindrical chamber 50 to accommodate at least a portion of the container 30 of the canister 26. One or more ribs 52 within the chamber 50 of the cylindrical portion 48 aid in locating and supporting the container 30 in an operable position within the actuator 28. The actuator 28 has a thumb button 54 disposed adjacent the support block 40.

As is typical, the aerosol dispensing assembly 25 is used to dispense a dosage of medication from within the container 30 by manual compression of the canister 26 and actuator 28 along the axis A. A force against the closed end 32 of the container 30 and an opposed force against the thumb button 54 of the actuator 28 trigger operation of the dispensing valve 34, causing the dispensing valve 34 to dispense a dose of medication through the elongate outlet member 36, orifice 46 and mouthpiece 44 for reception by a user.

Dose Counter Device

Figure 3:
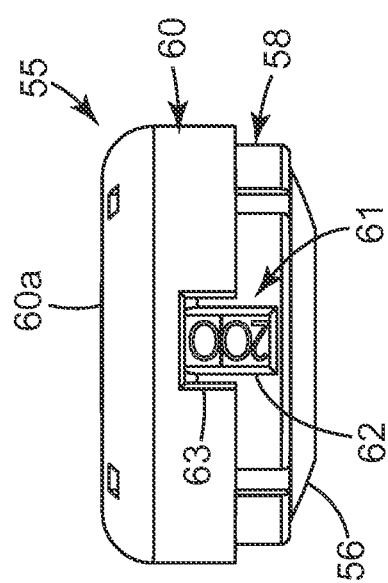

While FIGS. 1 and 2 show typical aerosol dispensing assemblies 25, these figures also illustrate a dose counter device 55 of the present invention. In the illustrated embodiment, the dose counter device 55 is connected to the canister 26 at the closed end 32 of container 30. Although any suitable means may be used to mount the dose counter device 55 to the canister 26 (e.g., adhesive, glue, tape, mechanical means, etc.) it is intended that once connected, those components become inseparable. Thus, up to a certain number of dosages, any dosage of medication dispensed from the canister 26 is monitored and counted by the dose counter device 55. As illustrated in FIG. 3, a bottom profile 56 of the dose counter device 55 may be convex in form to mirror a concave shape of the closed end 32 of the container 30 (such as concave shape 32a shown in phantom in FIG. 2). As further illustrated in FIG. 4, the dose counter device 55 is substantially cylindrical in form, and thus may be positioned as an add-on or extension of the container 30, at its closed end 32. Addition of the dose counter device 55 in this manner does not require any modification of the actuator 28.

The dose counter device 55 comprises a base 58 and a cap 60 slidably mounted onto the base 58. In one embodiment, an outer cylindrical profile of the base 58 is substantially similar in diameter to the outer cylindrical profile of the container 30 (as illustrated in FIGS. 1 and 2). In addition, the cylindrical and bottom profiles of the dose counter device 55 are, in one embodiment, shaped to mate with the closed end 32 of container 30, with minimal gaps at the interface therebetween. The base 58 is fixed to the container 30, while the cap 60 may move (as explained below) relative to the base 58 and container 30. The cap may be formed, as shown in FIG. 3, to enshroud other components of the dose counter device, partially or completely, or alternatively (not shown) it can be envisaged that the base might be formed to enshroud the other components of the dose counter.

The dose counter device 55 has dose counting indicia (illustrated generally as at 61) which change each time a user administers a dose of medication from the aerosol dispensing assembly 25, to indicate to the user the number of medication doses left in the container 30. In the illustrated embodiment, the indicia 61 are internal to the dose counter device 55, but are visible to a user through openings 62 and 63 in the base 58 and cap 60, respectively. In one embodiment, for example, the dose counter device 55 will indicate the number of doses remaining in the container 30 from two hundred doses (as shown in FIGS. 3 and 4) to zero doses. Each administration of a dose of medication is counted by the dose counter device 55 through the reciprocal motion of the cap 60 relative to the base 58 along the axis A. As the user administers a dose of medication from the aerosol dispensing assembly 25, the user pushes down on a top surface 60a of the cap 60, causing the cap 60 to move downwardly relative to the base 58 (as viewed in FIGS. 1 and 2), and causing the canister 26 to move downwardly relative to the support block 40 to release a dose of medication (assuming that a counterforce is applied on the actuator 28, such as on thumb button 54). On release of the compression force along axis A, the cap 60 is biased to return to its original non-depressed position (as illustrated in FIG. 3) thereby completing a count cycle of medication dose administration.

Figure 7:
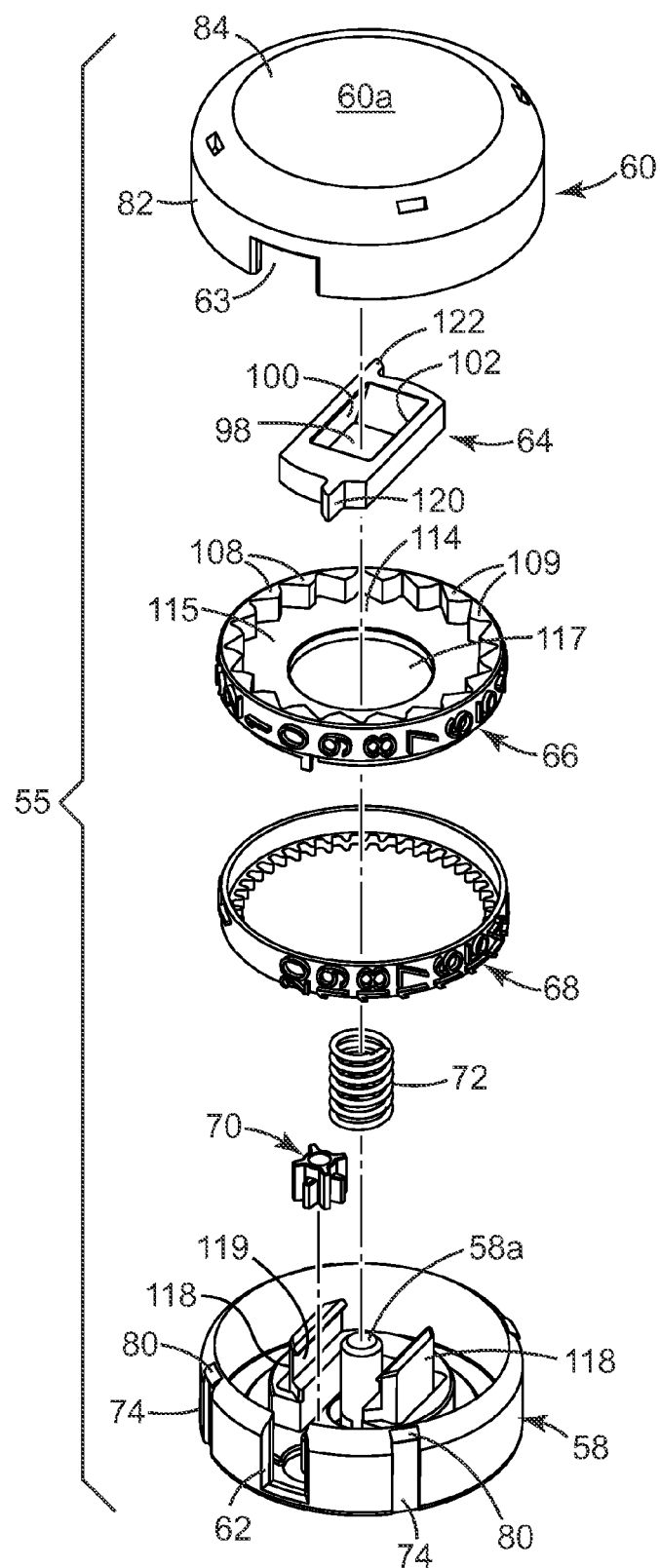
Figure 8:
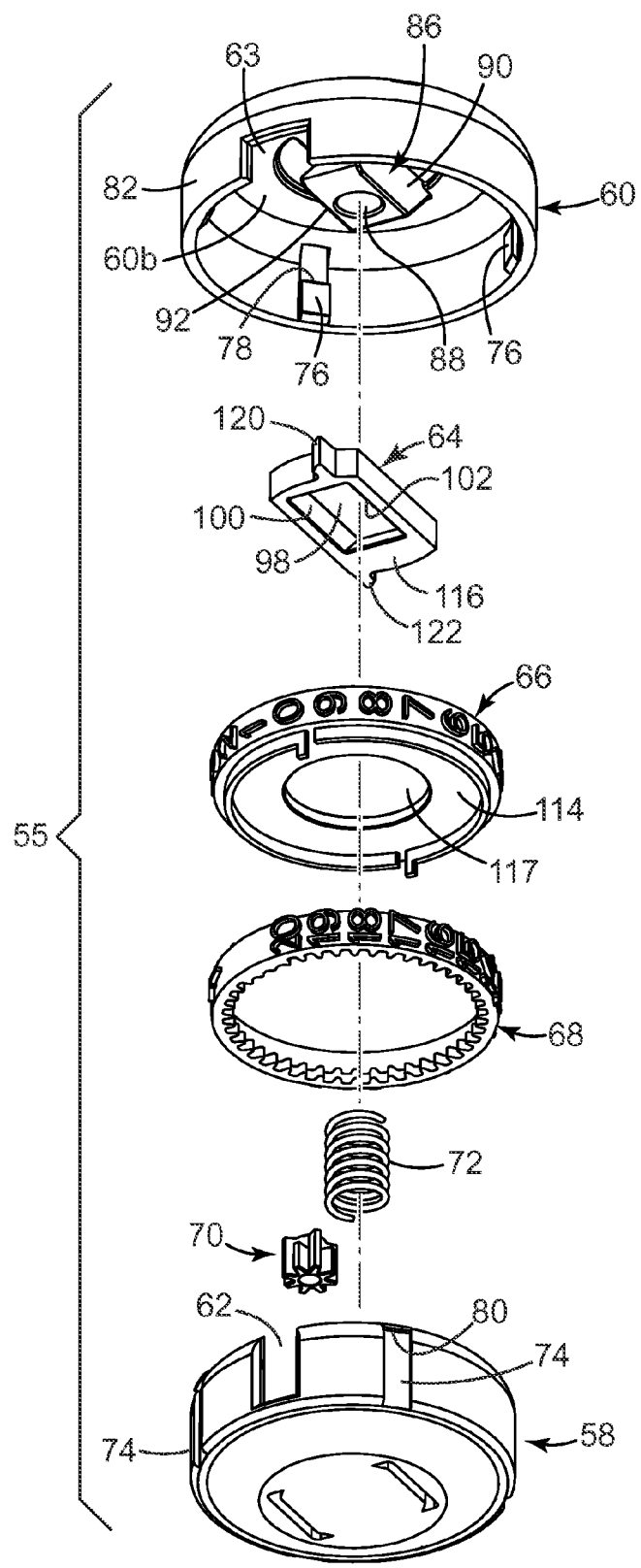

The inner components of the dose counter device 55, and in part their relationships, are illustrated in FIGS. 5, 6, 7 and 8. FIG. 5 illustrates the dose counter device 55 with the cap 60 removed for clarity of illustration. FIG. 6 illustrates the dose counter 55 with the cap 60 and additional components therein removed for clarity of illustration. FIG. 7 is an axially exploded isometric view, taken from an upper perspective of the components of the dose counter device 55. Dose counter device 55 includes the base 58 and the cap 60, along with a slider 64, a first counter or units ring 66, a second counter or tens ring 68, a transfer gear 70 and a spring 72. FIG. 8 illustrates these components in axially exploded isometric view, as taken from a bottom perspective thereof.

Figure 23:
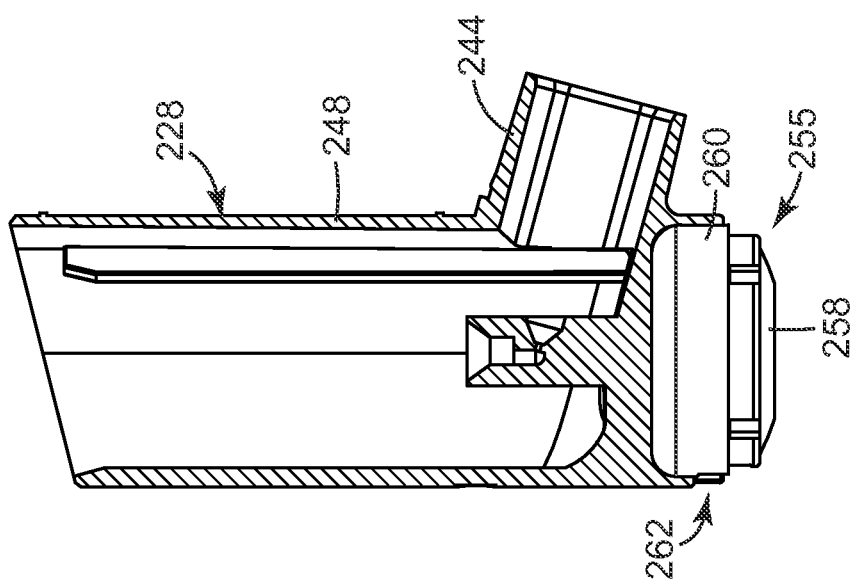
Figure 22:
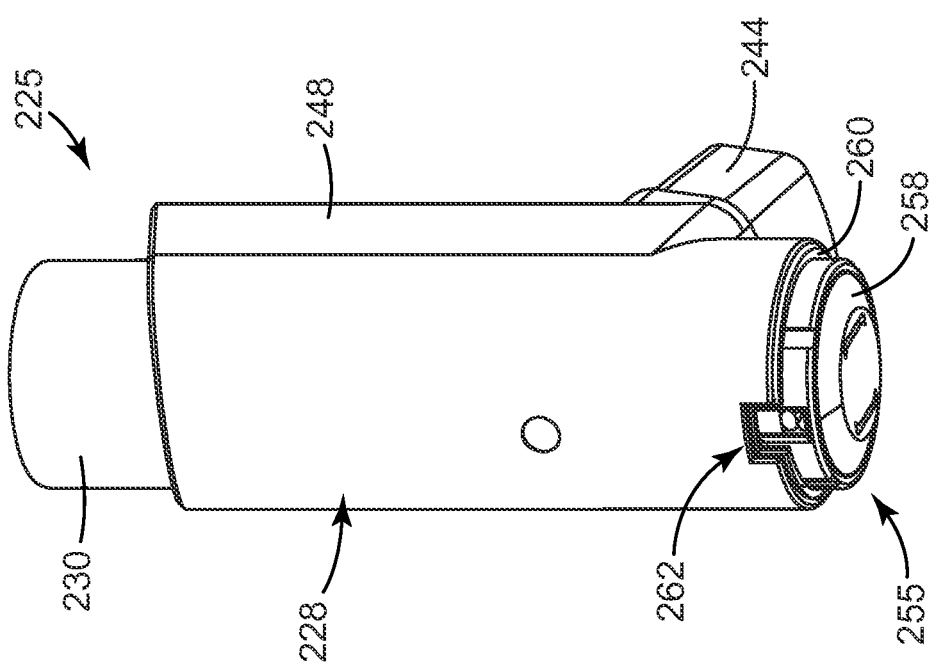

FIG. 22 shows another aerosol dispensing assembly 225, but fitted in an alternative manner with a dose counter device 255 of the present invention. The aerosol dispensing assembly comprises an actuator 228 comprising a mouthpiece 244 and an elongate portion 248 in the form of a generally cylindrical chamber to accommodate at least a portion of a medicament containing container 230. The dose counter device 255 comprises a cap 260 and a base 258, the cap being mounted on or within, or being integrally formed with, the lower end (in the orientation shown) of the actuator 228. Dose count indicating indicia are visible through opening 262. FIG. 23 shows the actuator 228 in section, relative to the dose counter device 255 disposed thereon. Again, the cap 260 may be affixed to or formed integrally with the actuator 228.

Axial Motion

The dose counter device 55, as illustrated in FIGS. 1 and 2, is positioned on the closed or top end of the aerosol canister 26. A user is required to push on top of the canister 26 to administer a dose of medication. As the dose counter device 55 is so pushed against the top of the canister 26, the cap 60 moves axially relative to the base 58 and indexes the first half of a count process (as further explained below). As the cap 60 moves, the aerosol medication canister 26 is also moved axially, relative to the actuator 28. The dose counter device 55 requires less force to operate it to make a count than is required to operate the dispensing valve 34 of the canister 26 to release a dose, thus ensuring that every dose of medication that is released from the container 30 is counted by the dose counter device 55. Once the compressive medication dispensing force is removed, both the dose counter device 55 and canister 26 return to their original positions, relative to the actuator 28 (see, e.g., FIGS. 1 and 2), although the visible indicia 61 then display a changed count.

The base 58 and cap 60 are affixed together to be non-rotatable relative to one another about the axis A, but to allow relative slidable movement axially. The base 58 has a plurality of axially parallel grooves 74 disposed about its circumference. The cap 60 has a like number of radially inwardly projecting detent features 76 which are formed to ride in the grooves 74. Once assembled, there is an interference between an upper edge 78 of each detent feature 76 and a shoulder 80 at a top end of each groove 74, thereby preventing separation of the base 58 and cap 60. The base and cap components are thus locked together, which prevents any tampering with the dose counter device components therein or with the measured count of dosages being tracked by the dose counter device.

Axial Motion Translated to Lateral Motion

Figure 9:
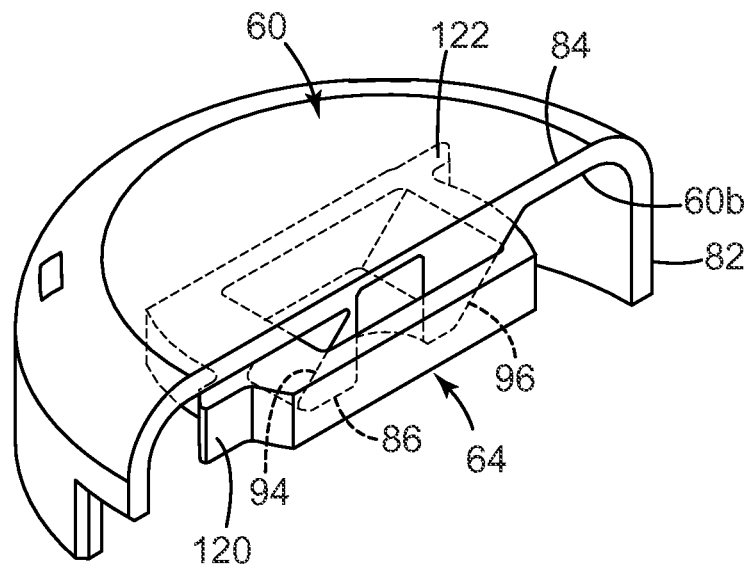
Figure 10:
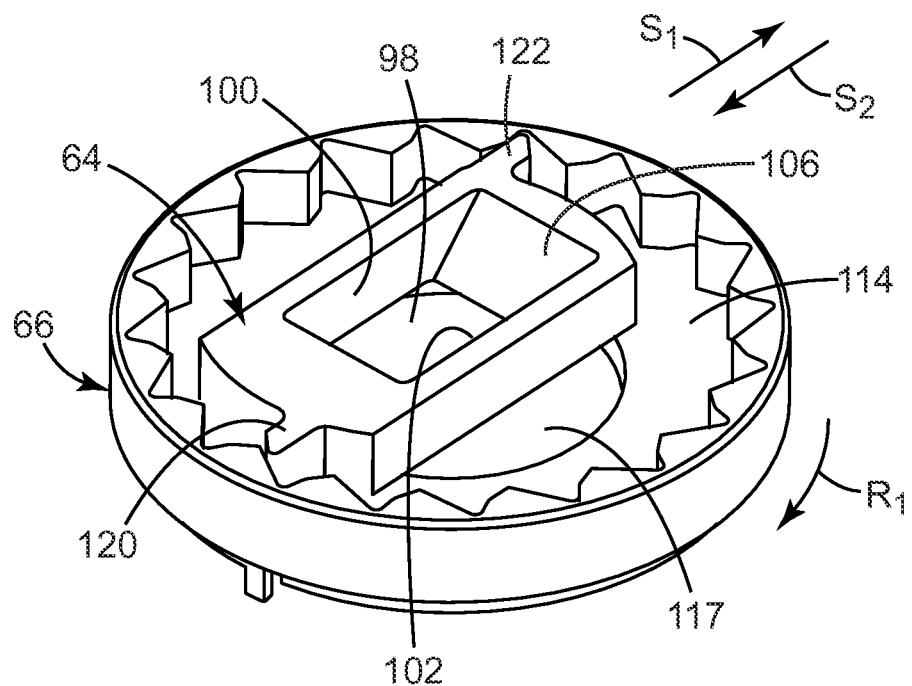

The cap 60 has a generally cylindrical outer wall 82 and an upper wall 84. A peg 86 extends centrally from the upper wall 84, within the cap 60, as illustrated in FIGS. 8 and 9. A central blind hole 88 extends into the peg 86 from a bottom side thereof toward the upper wall 84 of the cap 60. The peg 86 is generally shaped as a parallelogram, having two operative parallel walls 90 and 92 which are generally perpendicular to a bottom transverse surface 60b of the upper wall 84 of the cap 60. The parallel walls 90 and 92 and bottom surface 60b are best seen in FIG. 8. The peg 86 also has walls 94 and 96 that are parallel to each other, but the walls 94 and 96 are oriented at a 45° angle relative to the axis A, as ramps. The orientation of walls 94 and 96 is illustrated in FIGS. 9, 11 and 12.

Figure 11A:
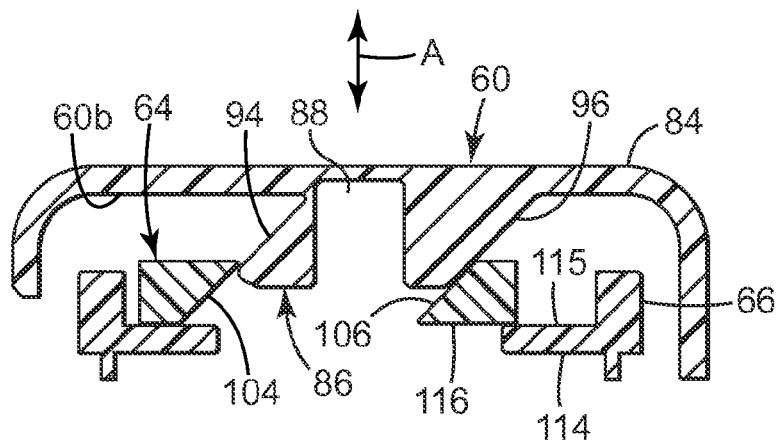
Figure 11B:
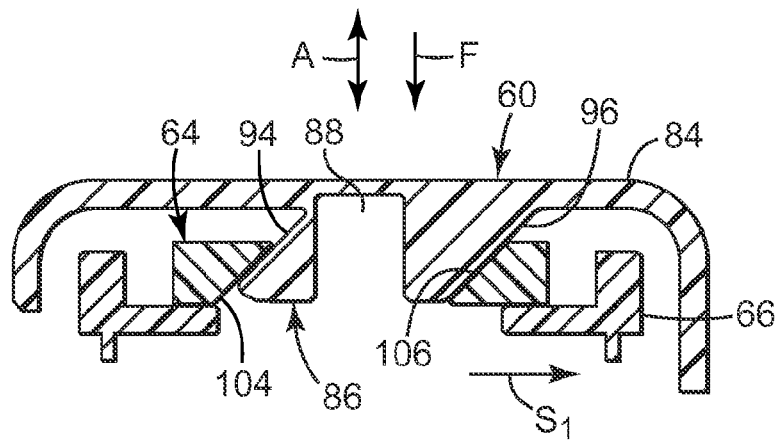
Figure 11C:
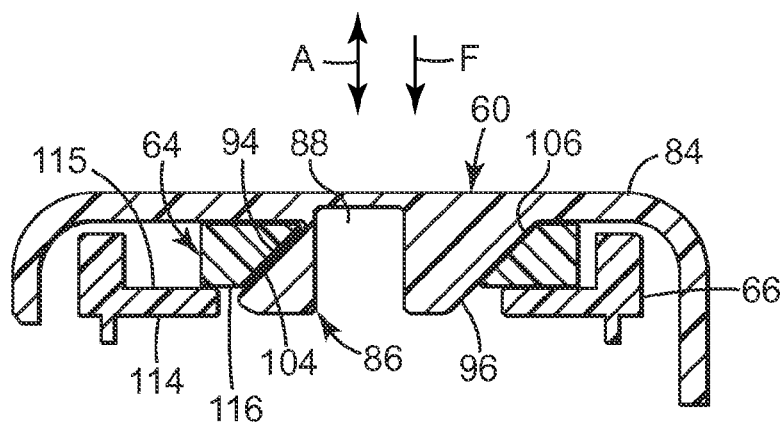

The slider 64 has an oblong hole 98 therethrough which is configured on its inner surfaces to slidably mate with the walls 90, 92, 94 and 96 of the peg 86 on the cap 60. Thus, the hole 98 of the slider 64 has, along its elongated dimension, opposed parallel walls 100 and 102, which are formed to slidably mate with the walls 90 and 92 of the peg 86. The slider 64 is thus configured to move transversely or laterally relative to the cap 60 and axis A. Likewise, the hole 98 of the slider 64 has walls or ramps 104 and 106 oriented at a 45° angle with respect to the axis A and configured to slidably mate with the walls 94 and 96 of the peg 86. FIGS. 11A, 11B and 11C show the movable relationship of the slider 64 and peg 86, as do FIGS. 12A, 12B and 12C.

Although in this embodiment the slider 64 is disposed about the peg 86, it will be clear to one skilled in the art that alternative embodiments can be envisaged in which one or more pegs are differently disposed relative to the slider. For example, a sliding surface could be provided on each of a pair of cantilevered protrusions, one on either side of the slider, cooperating with a pair of pegs on the cap 60.

Figure 12A:
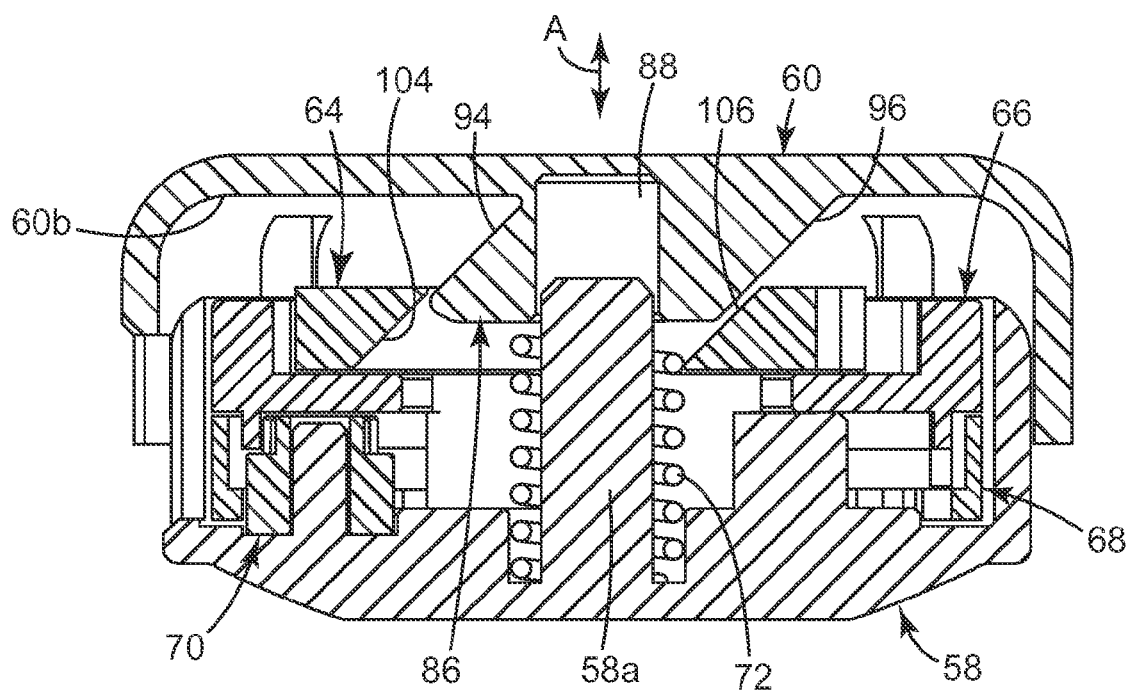

When no axial compressive force is applied, the cap 60 is biased away from the slider 64 by the compression spring 72 (as explained below) to a position as illustrated in FIGS. 11A and 12A. The slider 64 is engaged by the peg 86, but spaced from the bottom surface 60b of the upper wall 84 of the cap 60. As a user pushes on the cap 60 to initiate a dose of medication (see, e.g., force arrow F in FIGS. 11B and 12B), the cap 60 moves downwardly, as illustrated by comparison in relative position of the cap 60 in FIGS. 11A and 11B and in FIGS. 12A and 12B). As a result of the movement of the cap 60, the slider 64 moves laterally relative to the peg 86 (in direction $S_1$) by engagement of the opposed walls 94 and 104 and 96 and 106 of the peg 86 and slider 64, respectively. When the cap 60 is fully depressed relative to the base 58 by a user (e.g., force arrow F in FIGS. 11C and 12C), the slider 64 has further moved laterally and is also now adjacent the bottom surface 60b of the upper wall 84 of the cap 60, as seen in FIGS. 11C and 12C. The slider 64 is further moved laterally through opposed contact of the 45° faces of the walls 94 and 104 and the walls 96 and 106, of the peg 86 and slider 64, respectively. Upon release of the force by a user in dispensing a medication, the relationship of the slider and peg move in reverse order under the influence of the spring 72, until the components are again positioned as seen in FIGS. 11A and 12A. Thus, axial motion of the cap 60 relative to the base 58 causes transverse or lateral motion of the slider 64. In one embodiment, the slider is centrally located, and this motion is radial motion relative to the axis A.

Figure 12B:
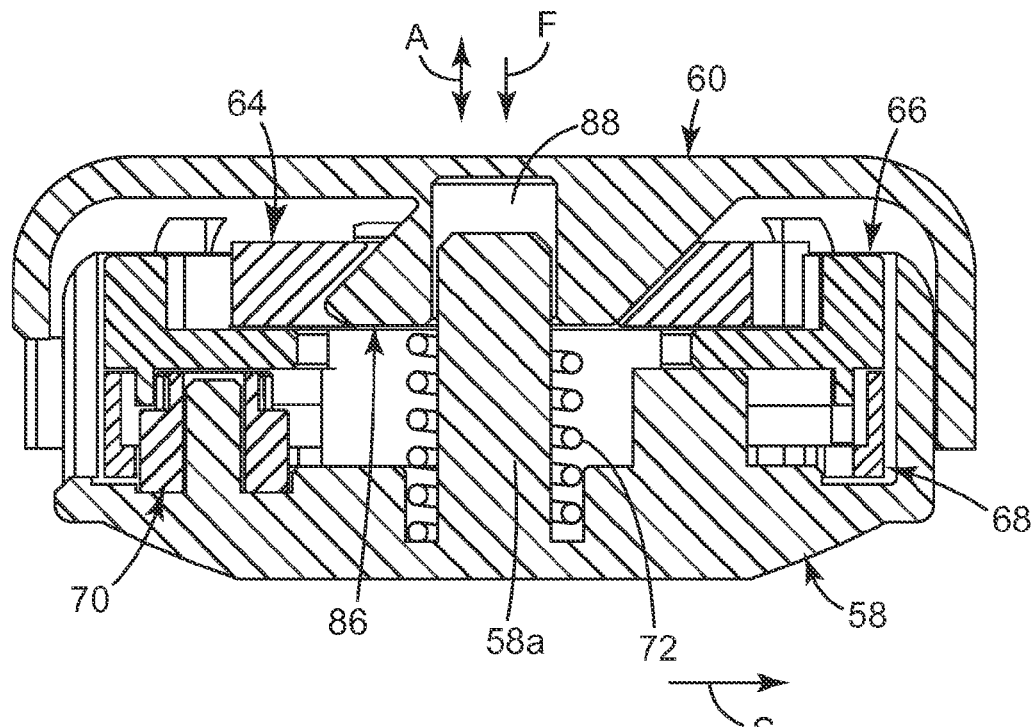
Figure 12C:
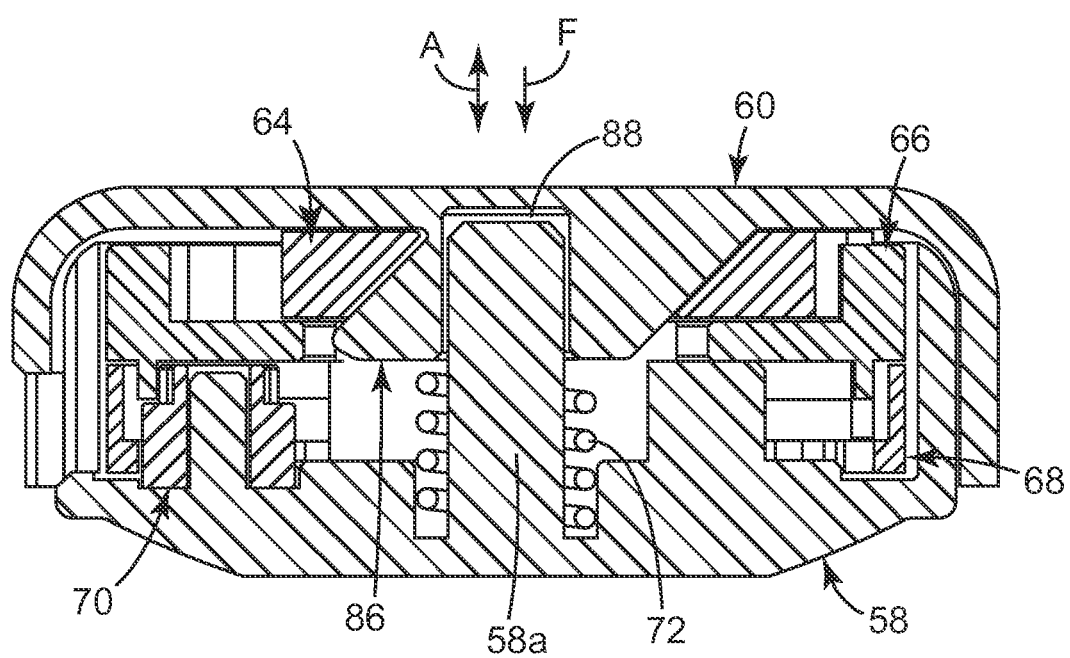

The relationship of the base 58 and the cap 60 during the downward stroke of a medication dispensing step is illustrated in FIGS. 12A, 12B and 12C. As noted above, the cap 60 is slidably mounted axially over the base 58. The base 58 has a central cylindrical post 58a which has its upper end received within the central blind hole 88 of the peg 86. The post 58a and blind hole 88 aid in aligning the cap 60 and base 58. The spring 72 is disposed between a bottom interior surface of the base 58 and a bottom of the peg 86. The spring is disposed about the post 58a and is compressed by user initiated forces for medication dispensing, as illustrated in FIGS. 12B and 12C. The spring 72 extends through intermediate components of the dose counter assembly between the cap and base, such as the slider 64, units ring 66 and tens ring 68, and normally biases the cap 60 and base 58 apart, to the position illustrated in FIG. 12A. The interfering upper edges 78 of the detent features 76 on the cap 60 and the shoulders 80 in the grooves 74 of the base 58 prevent separation of the cap 60 from the base 58.

Lateral Motion Translated into Rotational Motion

As illustrated by FIGS. 5, 10, 11, 12 and 13, the slider 64 is disposed within the units ring 66. The units ring 66 is generally cylindrical and has units numerical indicia on an outer cylindrical face thereof. The indicia are readily visible, and may be in any form, such as printed or formed thereon. In one embodiment, the indicia comprise the range of numbers zero through 9, disposed in series twice about the outer cylindrical face of the units ring 66. Around an inner circumferential surface thereof, the units ring 66 has a plurality of profiled teeth 108. Each tooth 108 has an advancing angle face 110 and second angled face 112. The units ring 66 also includes a lower wall 114. The lower wall 114 has a generally planar surface 115 that supports a bottom, generally planar face 116 of the slider. The lower wall 114 also has a central aperture 117 therethrough. As the slider thus moves transversely relative to the cap 60 (as illustrated in FIGS. 11A and 11B), it slides along the generally planar face 115 of the units ring 66.

The units ring 66 is rotatable with respect to the base 58, cap 60 and slider 64, in a plane perpendicular to the axis A and about the axis A. The slider 64 cannot rotate, however, since it is laterally slidably mated to the peg 86 on the cap 60. In addition, the slider 64 is constrained by a pair of guide panels 118 that project upwardly from the base 58. Each guide panel 118 has a transverse recess 119 formed therein for receiving the body of the slider 64, and each recess has an overhang 119a to retain the slider 64 within the recess 119. The central aperture 117 is large enough to accommodate the guide panels 118 projecting therethrough, as seen in FIG. 5. The slider 64 is thus nested within the units ring 66 and constrained to move reciprocally in a linear direction, as illustrated by direction arrows $S_1$ and $S_2$ in FIGS. 10, 11 and 13, generally in the same plane as the units ring 66 rotates about the axis A.

The slider 64 has two fingers 120 and 122 projecting outwardly therefrom, generally along the direction of slider linear movement, from each end of the slider 64. The fingers 120 and 122 are, in one embodiment, asymmetrically aligned on the slider 64, relative to the axis A. Each finger is formed to engage and be received between the teeth 108 of the units ring 66. The linear reciprocal motion of the slider 64 is translated into rotational motion of the units ring 66 by interaction of the fingers 120 and 122 in the teeth 108. The teeth on the units ring are engageable by the fingers of the slider alternatively to cause indexed rotation of the units ring with respect to the base. Before one finger moves out through the arc traversed by the tips of the teeth 108 on one side of the units ring 66, the other finger moves in through the arc traversed by the tips of the teeth 108 on the other side of the units ring, thus making it impossible for the units ring ever to rotate freely as may be seen from FIGS. 13B and 13D. In addition, this arrangement avoids the need to provide a separate anti-reverse ratchet for the units ring 66.

The asymmetrical nature or positioning of the fingers 120 and 122 allows the slider to operate with a units ring 66 with an even number of teeth 108, necessary for satisfactory counting in Base Ten counting systems.

The sequence of one reciprocating movement of the slider and the resultant rotational movement of the units ring through an arc equal to one count of a single dosage of medication is illustrated in FIGS. 13A-13E. FIG. 13A corresponds to the position of the slider 64 relative to the units ring 66 illustrated in FIGS. 11A and 12A. The units ring can be defined as at position $P_1$ relative to rotational movement about axis A. As motion of the cap 60 downwardly toward the base 58 is translated into transverse motion of the slider 64 by the opposed ramped surfaces 94, 104 and 96, 106, respectively, the finger 120 of the slider 64 leaves engagement with a notch between the advancing angle face of the tooth 108a and the second angled face of the tooth 108c of the units ring, while the finger 122 engages the advancing angle face of the tooth 108b of the units ring 66. The orientation of the slider 64 relative to the cap 60 and its transverse motion in direction $S_1$ is illustrated in FIGS. 11B and 12B, and corresponding FIG. 13B. Note that at this time, the units ring 66 has not begun to rotate (i.e., position $P_1$ is the same in FIG. 13B as in FIG. 13A). When the cap 60 is fully depressed relative to the base 58, the slider 64 has been fully moved transversely to the position illustrated in FIGS. 11C and 12C (and in corresponding FIG. 13C). In this position, the finger 122 is now fully seated into a notch between the advancing angle face of the tooth 108b and the second angled face of the tooth 108d of the units ring 66, as seen in FIG. 13C. Engagement of the finger 122 with the advancing angle face of the tooth 108b causes the units ring 66 to rotate clockwise (see arrow $R_1$ in FIG. 13C) to position $P_2$, representing a change in orientation of arc $\alpha$ relative to axis A, as illustrated in FIG. 13C. This movement in a circumferential direction represents approximately one half of a count motion of the units ring 66 relative to the non-rotatable base 58 and cap 60.

Once the force F (see FIGS. 11C and 12C) is released, the spring 72 urges the cap 60 away from the base 58 and, as the cap 60 moves, the slider 64 moves in lateral direction $S_2$ (in opposite linear direction to direction $S_1$) as illustrated in FIG. 13D. The finger 122 leaves engagement with the notch between teeth 108b and 108d, while at the same time the finger 120 engages the advancing angle face of the tooth 108c. Although the motion of the slider 64 is reversed, the relative orientation of components in FIG. 13D is generally similar to that illustrated in FIGS. 11B and 12B. Upon the cap 60 being fully pushed away from the base 58 by the spring 72, the slider 64 transversely returns to its original position (i.e., its position in FIG. 13A), but now its finger 120 is disposed in the notch between the advancing angle face of the tooth 108c and the second angled face of the tooth 108e. Engagement of the finger 120 with the advancing angle face of the tooth 108c causes the units ring 66 to rotate further clockwise (see arrow $R_1$ in FIG. 13E) to position $P_3$, representing another approximately one half count motion, and thus completing a single unit count of the units ring 66 movement through arc $\beta$ relative to axis A (with arc $\beta$ approximately equal to two arcs $\alpha$), as seen in FIG. 13E. The orientation of components in FIG. 13E corresponds generally to that illustrated in FIGS. 11A and 12A, and thus the dose counter device 55 has recorded a count for the latest dose of medication dispensed, and is ready for counting the next dosage of medication dispensed from container 30. At no time during the shuttling back and forth of the slider 64 within the units ring 66 does the units ring 66 become free to rotate relative to the slider 64. The slider 64 always has at least one of its fingers 120 or 122 within the region traversed by the teeth 108 of the units ring 66, and thus the units ring 66 can only rotate when permitted to do so by relative transverse movement of the slider 64.

This arrangement thus provides an elegant and low profile means for translating the axial motion of the cap 60 into lateral motion of the slider 64, and then rotational motion of the units ring 66. This nested arrangement of components provides a dose counter device 55 having a relatively low profile (along axis A), which is useful to accommodate users having smaller hands so that the application of force between the top surface 60a of the cap 60 and a bottom surface of the actuator 28 (such as thumb button 54) is linearly spaced apart as small a distance as possible.

Rotational Motion Translated into Another Rotational Motion

As noted above, the units ring 66 has single unit indicia thereon (see, e.g., FIGS. 7 and 8). In order for the dose counter device 55 to count higher numbers of dosages, a tens ring 68 is provided with units indicating different decades of count (see, e.g., FIGS. 7 and 8). The tens ring 68 is generally cylindrical and has the tens numerical indicia on an outer cylindrical face thereof. Like the units ring 66, the indicia on the tens ring 68 are readily visible, and may be in any form, such as printed or formed thereon. For instance, the dose counting indicia 61 illustrated in FIG. 3 is the number "200" with a "20" illustrated on the tens ring 68 and a "0" illustrated on the units ring 66. After one dosage of medication has been dispensed by the aerosol dispensing assembly 25 with the dose counter device 55 thereon, the dose counting indicia visible would be number "199", with a "19" exposed on the tens ring 68 and a "9" exposed on the units ring 66. After a next dosage, the visible number would be "198", and so on until the dose counter indicia reach zero counts (e.g., the indicia show "000" to a user). It will be appreciated to one skilled in the art that alternatively the dose counter could count up (i.e. indicate doses used, rather than doses remaining). Alternatively again, the indicia could comprise colored bands or other markings, rather than numerals.

Figure 16:
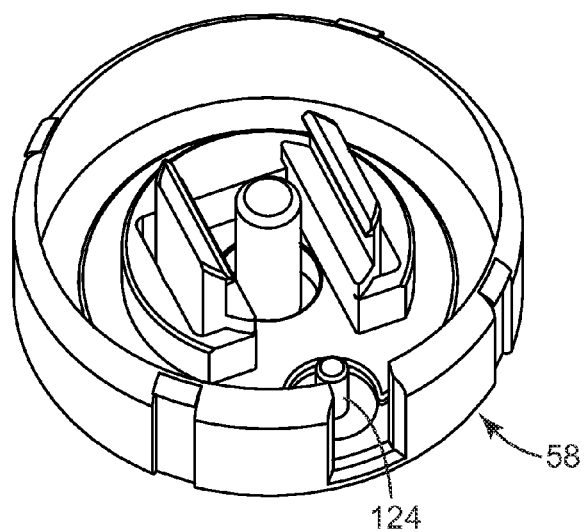
Figure 17A:
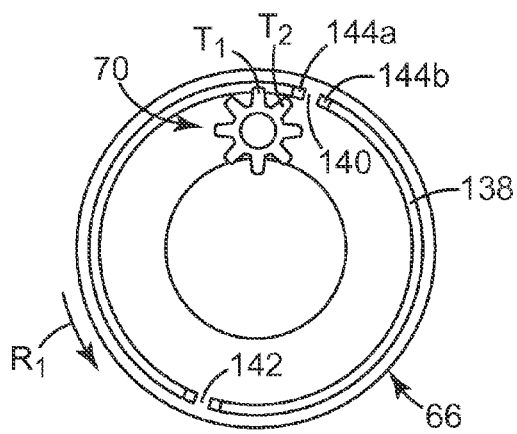
Figure 17B:
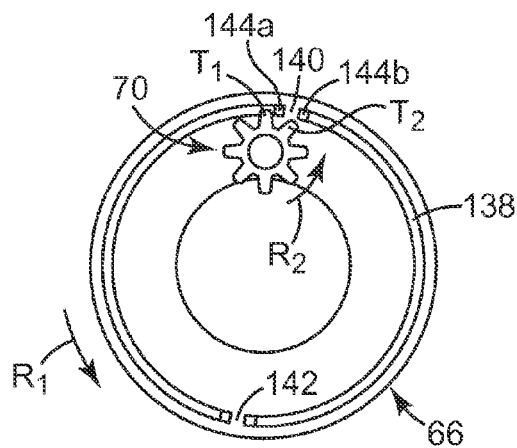
Figure 17C:
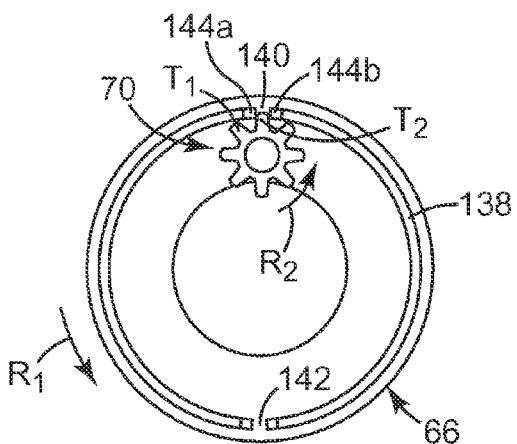
Figure 17D:
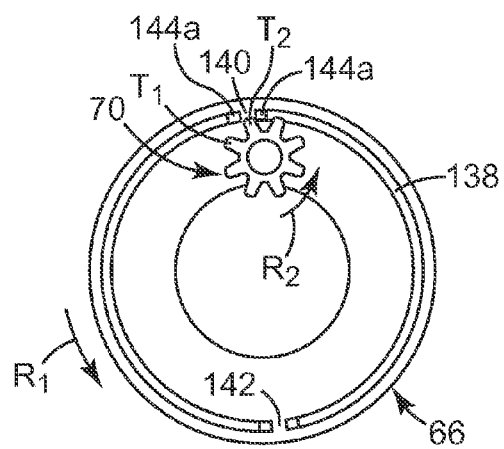
Figure 17E:
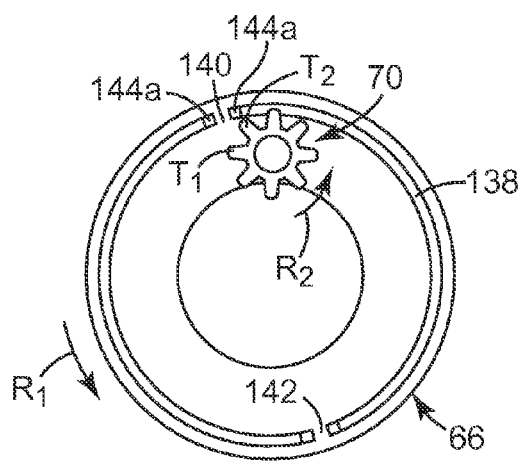

Rotational movement of the units ring 66 is translated into rotational movement of the tens ring 68 by means of the transfer gear 70 therebetween. The transfer gear 70 has a central bore 123 which is rotatably disposed about a spindle 124 extending upwardly from the base 58 (see FIGS. 6 and 16), on an axis parallel to the axis A. The transfer gear 70 is disposed between the units ring 66 and the tens ring 68 and aligned to cause rotation of the tens ring 68 as a function of the rotation of the units rings 66. The transfer gear 70 is formed as a two-tier cog, with an upper tier having a first plurality of gear teeth (e.g., four teeth) and a lower portion having a second plurality of gear teeth (e.g., eight teeth, with four of the eight teeth of the second plurality being continuations of the four teeth of the first plurality). Accordingly, the transfer gear 78 has a first plurality of tall teeth 132 and a second plurality of shorter teeth 134.

Figure 14:
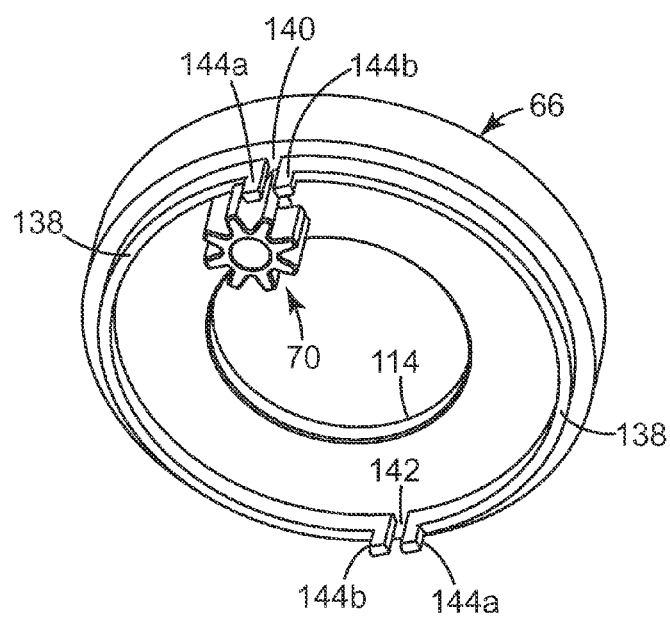
Figure 15:
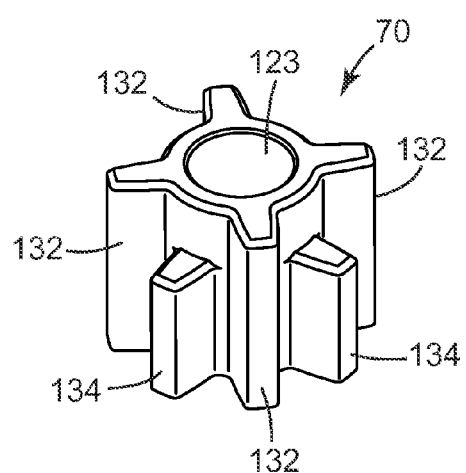

The lower wall 114 of the units ring 66 has a generally planar bottom face 136, and an annular rim 138 extends downwardly from the bottom face 136, spaced radially inwardly from the outer cylindrical face of the units ring 66. As seen in FIG. 14, the rim 138 has slots 140 and 142 disposed therein. Adjacent to each slot, the rim 138 has a pair of legs 144a and 144b projecting downwardly therefrom. The slot 140 is provided for each time that a change in the decade count is to be made by the dose counting indicia. The legs 144a and 144b project downwardly to engage not only the tall teeth 132 of the transfer gear 70, but also the shorter teeth 134 thereof. Whenever one of the tall teeth 132 on the transfer gear becomes disposed within the slot 140 in-between the legs 144a and 144b, it is carried by rotation of the units ring 66 to rotate the transfer gear 70. While two slots and associated legs are shown, it is contemplated that in alternative embodiments there may be only one slot and pair of legs, or there may be more than two.

The translation of rotation from the units ring 66 to the transfer gear 70 is illustrated in FIGS. 17A to 17E. Rotation of the units ring 66 is again illustrated by arrow $R_1$, while rotation of the transfer gear 70 is illustrated by arrow $R_2$. As a leg 144 is moved by rotation of the units gear 66 into engagement with a tooth $T_1$ (one of the shorter teeth 134) of the transfer gear 70 (see FIG. 17B), it causes rotation of the transfer gear 70, bringing tooth $T_2$ (one of the tall teeth 132) into the slot 140 (see FIG. 17C). As the units ring 66 continues to rotate, the leg 144b causes the tooth $T_2$ of the transfer gear 70 to continue to move or rotate (see FIG. 17D), until it is clear from the leg 144b (see FIG. 17E). (As will become evident from a study of FIGS. 18A to 18E, tall tooth $T_2$ is also moved by engagement in slot 140 in annular rim 138, so leg 144b is not strictly required.) In doing so, the transfer gear 70 has thus been rotated from the position illustrated in FIG. 17A to the position illustrated in FIG. 17E (comparing the respective positions of teeth $T_1$ and $T_2$ in FIGS. 17A and 17E). This sequence thus rotates the transfer gear 70 a quarter rotation, in the embodiment illustrated.

Figures 18A, 18B:
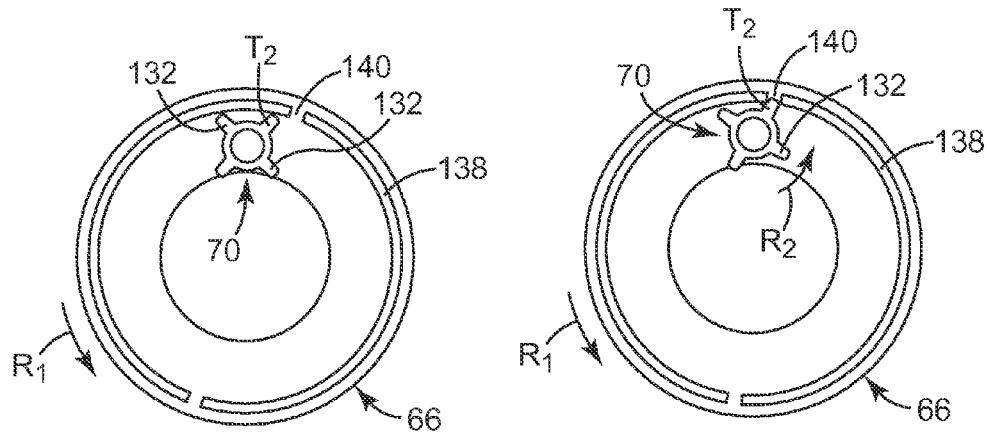
Figures 18C, 18D:
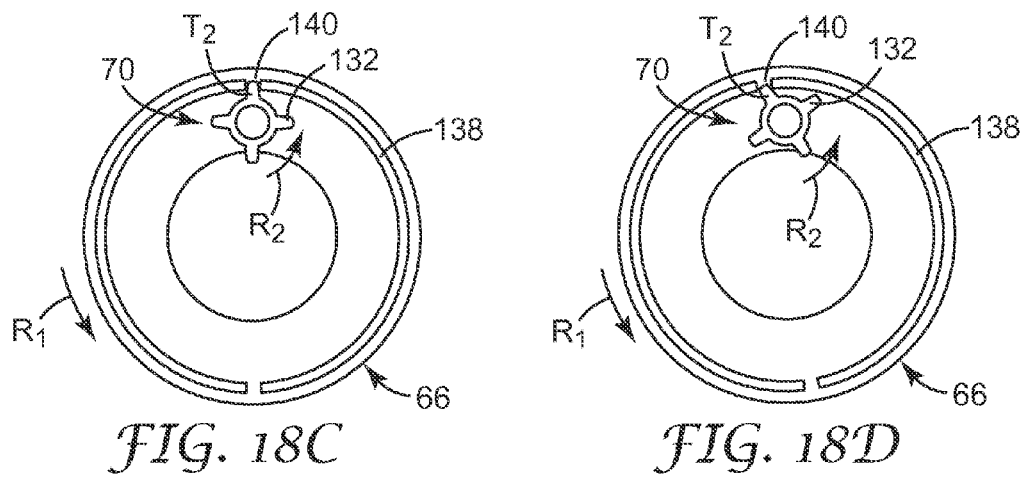
Figure 18E:
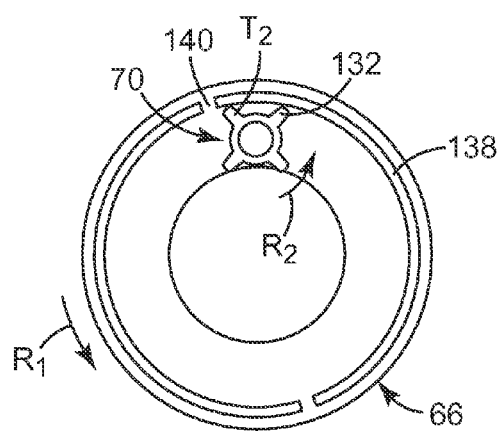

FIGS. 18A to 18E illustrate a further relationship between the transfer gear tall teeth 132 and the annular rim 138 on the units ring 66. In FIG. 18, only the tall teeth 132 are illustrated on the transfer gear 70 for clarity. The tall teeth 132 interfere with the rim 138 to prevent rotation of the transfer gear 70, except in those instances when a tall tooth 132 is engaged by the slot 140 (or another slot, such as the slot 142). As illustrated by FIGS. 18A and 18E, unless a tooth 132 of the transfer gear 70 is in engagement with one of the slots, the transfer gear 70 is constrained from movement by interference of the teeth 132 with an inner circumferential surface of the annular rim 138.

The tens ring 68 has, on an inner circumferential surface, a plurality of teeth 150 which are formed to engage with the teeth 132 and 134 of the transfer gear 70. The relationship between the transfer gear teeth and the teeth of the tens unit is illustrated in FIGS. 6, 19, 20 and 21. The eight teeth 132 and 134 of the transfer gear 70 are all in engagement with the teeth 150 of the tens ring 68. Thus, whenever the transfer gear 70 is caused to be rotated by rotation of the units ring 66, its rotation is transferred to the tens ring 68. A quarter turn of the transfer gear 70 causes rotation of the tens ring 68 (in direction of rotation arrow $R_3$ in FIG. 21A) sufficient to change the tens (decades) digit or digits that are visible to a user.

Figure 21A:
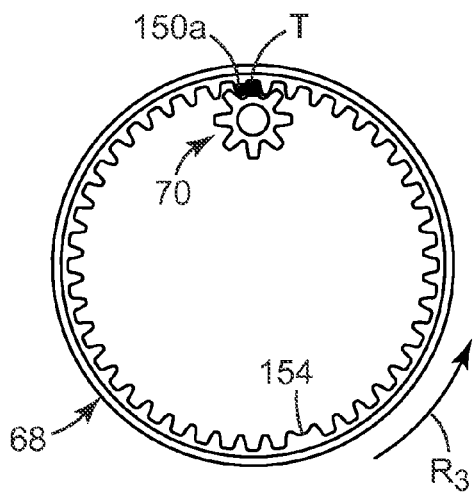
Figure 21B:
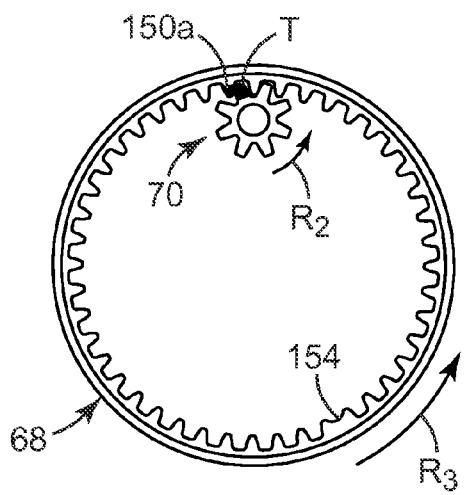
Figure 21C:
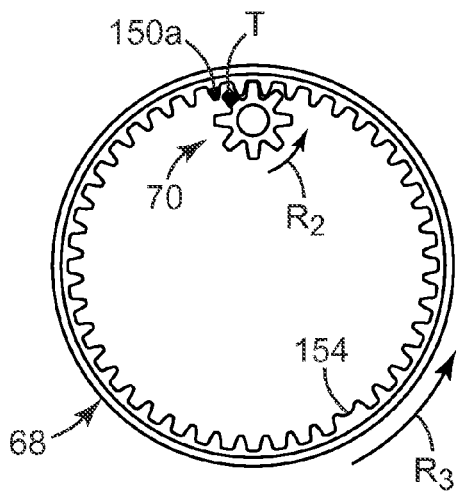
Figure 21D:
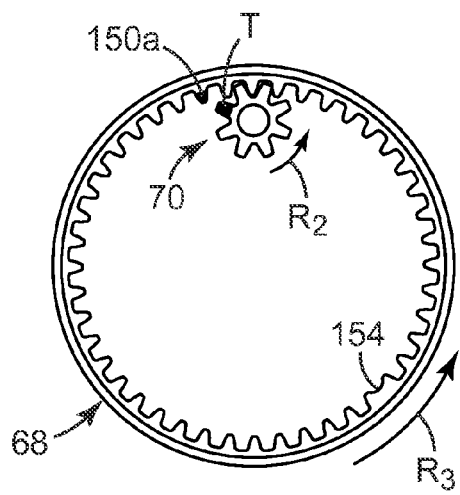
Figure 21E:
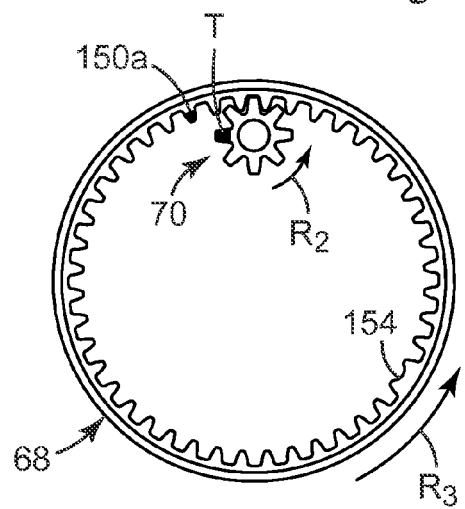

FIGS. 21A-21E illustrate a sequence of change of the tens ring 68 from one decade to another, through a quarter rotation of the transfer gear 70. For illustrative purposes, one of the teeth 150 of the tens ring 68 is illustrated as tooth 150a, which, in FIG. 21A is adjacent a tooth T of the transfer gear 70. As the transfer gear 70 is rotated in direction $R_2$, as illustrated in FIG. 21B, the engagement of the teeth of the transfer gear 70 and the teeth of the tens unit 68 cause rotation of the tens unit 68 in direction of $R_3$. As the transfer gear 70 continues to rotate during the administration of one dosage of medication, the transfer gear 70 completes a quarter turn rotation, which causes the exemplary tooth 150a on the tens ring 68 to move to the position shown in FIG. 21E. At the same time, the exemplary tooth T on the transfer gear 70 has rotated a quarter turn in direction $R_2$. The consequence of this rotation of the tens ring 68 is to change the decade digit on the outer circumferential surface of the tens ring 68 that is visible to a user. In a count down mode, this happens whenever a zero is changed to a nine on the units ring 66.

One or more cavities between adjacent teeth 150 on the tens ring 68 are filled. Thus, when the tens ring 68 reaches the "zero" position (indicating, for example, that two hundred doses of medication have been administered from the aerosol container) this filled in tooth area (illustrated as area 154 in FIGS. 19 and 21) stops the transfer gear 70 from further rotation. This in turn prevents the units ring 66 from rotation, which in turn prevents the slider 64 from its full movement, and in turn locks the cap 60 from being fully depressed relative to the base 58. When in this locked up position, the dose counter device 55 will no longer count doses of medication administered from the aerosol dispensing assembly 25. However, the aerosol dispensing assembly 25 may still be used to dispense medication if there is any medication left in the container 30. The dose counter device 55 is locked up, so that a user can still press on it to activate the medication dispensing valve 34 and release medication from the container 30.

If a user only depresses the cap 60 by a distance insufficient to fully operate the dose counter device 55, and then releases the cap, there is a small chance that the slider 64 will be unable to return to its full extent of return travel in direction $S_2$ due to finger 120 meeting "tooth to tooth" with the tip of a tooth 108 of the units ring 66. This problem will, however, be overcome upon the next proper depression of the cap 60. The converse potential problem, of finger 122 meeting "tooth to tooth" with a tooth 108 as a result of incomplete release of the cap 60, will be correspondingly overcome upon the next proper release of the cap.

Figure 19:
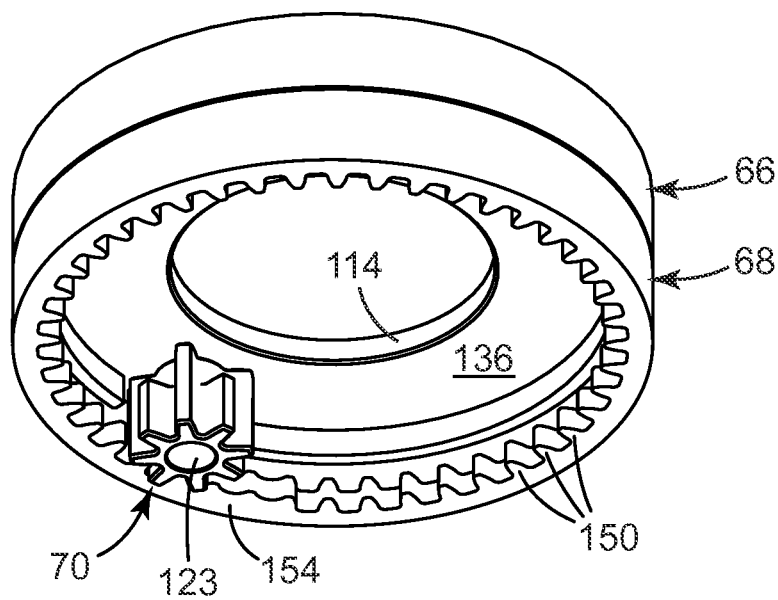
Figure 20:
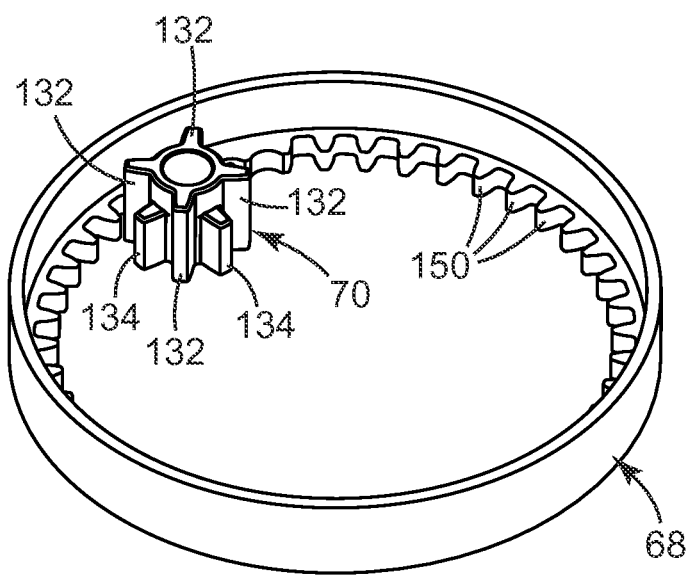

As illustrated in FIGS. 6 and 12, the tens ring 68 has a relatively low profile and is seated within the base 58 and about the transfer gear 70. The units ring 66 is rotatably disposed (coaxially) directly above the tens ring 68 as illustrated in FIG. 19. Again, the close interfitting and low profile nature of the dose counter device 55 of the present invention and its components facilitates use thereof by users with smaller hands.

In other aspects of the present invention, a mechanical dose counter, for counting doses of an aerosol medication dispensed from an aerosol dispensing assembly (e.g. a metered dose inhaler), whereby the dispensing is caused by an application of a force in the axial direction on the assembly (e.g. by manual compression of a canister and an actuator of a metered dose inhaler along axis A) and operable by application of a force in the axial direction to the assembly, is mounted onto or integral with the external end of the housing (e.g. an actuator of a metered dose inhaler) that is opposite to the closed end of the container (e.g. a canister of a metered dose inhaler).

As can be appreciated from FIG. 22, such an operable dose counter (e.g. a dose counter 255 as described above) may be mounted on the actuator housing 228 of an aerosol dispensing assembly 225, or alternatively the dose counter may be integral with the actuator housing, at a position on the external end of the actuator opposite to the closed end of the canister 230. Such a position confers advantages. For example, incorporation at the bottom end (in the orientation shown in FIGS. 22 and 23) of the actuator housing facilitates handling and ease of use by users, especially users, like children, with smaller hands. There are also manufacturing and logistical advantages of combining the dose counter and the actuator housing in this way. For example, there is no need to align and reliably affix a dose counter base, which might preferably be an injection molded plastic component, onto a metal container base, and in addition less plastic material may be required. In addition, such an arrangement offers the potential benefit that the dose counter cannot interfere with the emerging medicament spray, which is a common problem with other actuator mounted (internal) dose counters.

In essence, the inventive dose counter device operates in the following fashion. The reciprocal axial motion of the cap relative to the base causes reciprocal lateral (e.g., radial) motion of the slider under the cap and within the units ring. The units ring is caused to rotate by engagement of its teeth with opposed fingers on the slider, as the slider reciprocates, with one complete back and forth motion of the slider equaling a single count change in position of the units ring. The back and forth motion of the slider corresponds to the up and down motion of the cap. Rotation of the units ring is translated into rotation of the tens ring via the transfer gear disposed between and within the two rings. However, the tens ring is only rotated periodically relative to the units ring, to indicate a change in decade of the counts (i.e., it is only moved once for every ten movements of the units ring). Each time the units ring counts ten counts, the tens ring is indexed one position.

Although the present invention has been described with reference to preferred embodiments, workers skilled in the art will recognize that changes may be made in form and detail without departing from the spirit and scope of the invention. For instance, orientation references used herein such as above, below, downwardly and the like are not intended to be limiting in nature, but only to provide visual references for the reader. It is understood that the dose counter device will function whether operated as illustrated in an upright orientation as in FIGS. 1-3, or in any other orientation (e.g., upside down). In addition, the use of subtitles herein is not intended to limit the scope of the disclosure or invention, but is done merely for the convenience of the reader.

What is claimed is:

1. A dose counter device of the type for use on an aerosol dispensing assembly, wherein the dose counter device is for indicating the release of a dose of aerosol medication caused by the application of a force, in an axial direction, on the aerosol dispensing assembly, the dose counter device comprising:
    a base;
    a cap coupled to the base for axial, non-rotational movement with respect to the base, with the cap having a peg thereon extending toward the base;
    a spring disposed between the base and the cap to bias the cap axially away from the base;
    a slider non-rotatably disposed relative to the peg, the slider having two fingers projecting from opposite ends thereof, the slider and the peg having cooperating facing and slidably mating surfaces whereby axial movement of the cap relative to the base causes lateral movement of the slider relative to the cap; and
    a first counter ring rotatably disposed relative to the base, the first counter ring having an inner surface comprising teeth that are engageable by the fingers of the slider acting alternately to cause indexed rotation of the first counter ring with respect to the base; and
    wherein the base or the cap is mountable to the aerosol dispensing assembly.

2. A dose counter device of claim 1, wherein the aerosol dispensing assembly comprises an aerosol container having a nozzle end and a closed end, and wherein the base or the cap, as applicable, is adapted to be mounted to the closed end of the container.

3. A dose counter device of claim 1, wherein the aerosol dispensing assembly comprises a container and a housing therefor, and wherein the base or the cap, as applicable, is adapted to be mounted to the housing of the aerosol dispensing assembly.

4. A dose counter device of claim 3, wherein the aerosol container has a nozzle end and a closed end and the base or the cap, as applicable, is adapted to be mounted to an external end of the housing that is opposite to the closed end of the container.

5. A dose counter device of claim 1, wherein an outer surface of the first counter ring bears indicia thereon which are disposed as a function of the indexed rotation of the first counter ring relative to the base, and the device has an aperture therethrough for viewing the indicia on the first counter ring.

6. A dose counter device of any claim 1, wherein the two fingers on the slider are asymmetrical.

7. A dose counter device of claim 1, wherein the facing sliding surfaces of the slider and peg are aligned at about a 45° angle relative to the axial direction.

8. A dose counter device of claim 1, wherein the slider is disposed substantially within the first counter ring.

9. A dose counter device of claim 1, wherein the first counter ring is disposed to rotate within a plane substantially perpendicular to the axial direction.

10. A dose counter device of claim 1, wherein the lateral movement of the slider occurs within substantially the same plane in which the first counter ring is disposed.

11. A dose counter device of claim 1, wherein the slider has an oblong hole therethrough for receiving the peg, with the hole's elongated dimensions extending along the direction of lateral movement of the slider.

12. A dose counter device of claim 1, wherein the slider has two spaced apart sliding surfaces that are generally parallel.

13. A dose counter device of claim 1, wherein the base has a pair of panels extending toward the cap, with the panels having facing parallel slots which extend in the direction of lateral movement of the slider.

14. A dose counter device of claim 1, wherein the slider has a hole therethrough for receiving the peg, and wherein the spring extends into the hole when the slider is in a first position relative to the cap.

15. A dose counter device of claim 14, wherein the hole in the slider is spaced from the spring when the slider is in a second position relative to the cap.

16. A dose counter device of claim 1, wherein the base has a post thereon extending coaxially toward the cap, and the peg of the cap has a coaxially disposed hole therein facing the base for slidably receiving the post.

17. A dose counter device of claim 1, wherein the first counter ring is rotatable about an axis, and wherein the slider is aligned to move radially relative to the axis.

18. A dose counter device of claim 1, and further comprising:
   a second counter ring rotatably disposed relative to the base; and
   a transfer gear disposed between the first counter ring and the second counter ring and aligned to cause rotation of the second counter ring as a function of the rotation of the first counter ring.

19. A dose counter device of claim 18, wherein the transfer gear is disposed within the first counter ring and the second counter ring.

20. A dose counter device of claim 18, wherein the transfer gear has a first plurality of gear teeth thereon, wherein the first counter ring has a generally annular rim disposed thereon, on a side of the first counter ring opposite the teeth thereof, and wherein the rim comprises at least one slot therethrough for coupled rotational engagement with one of the gear teeth of the first plurality of gear teeth on the transfer gear.

21. A dose counter device of claim 20, wherein the rim has at least one leg adjacent to each slot to facilitate rotation of the transfer gear.

* * * * *

UNITED STATES PATENT AND TRADEMARK OFFICE
CERTIFICATE OF CORRECTION

| | | |
|---|---|---|
| PATENT NO. | : 8,517,019 B2 | Page 1 of 1 |
| APPLICATION NO. | : 12/281559 | |
| DATED | : August 27, 2013 | |
| INVENTOR(S) | : Richard D. Brewer et al. | |

It is certified that error appears in the above-identified patent and that said Letters Patent is hereby corrected as shown below:

In the Specification

Column 1
Line 8, "2008" should read --2007--.

Column 10
Line 48, "thereof" should read --thereof.--.

In the Claims

Column 14
Line 41, delete "any".

Signed and Sealed this
First Day of April, 2014

Michelle K. Lee
*Deputy Director of the United States Patent and Trademark Office*